United States Patent
Sarvazyan

(10) Patent No.: US 8,649,875 B2
(45) Date of Patent: *Feb. 11, 2014

(54) SYSTEMS FOR REMOTE GENERATION OF ELECTRICAL SIGNAL IN TISSUE BASED ON TIME-REVERSAL ACOUSTICS

(75) Inventor: Armen P. Sarvazyan, Lambertville, NJ (US)

(73) Assignee: Artann Laboratories Inc., Trenton, NJ (US)

(*) Notice: Subject to any disclaimer, the term of this patent is extended or adjusted under 35 U.S.C. 154(b) by 8 days.

This patent is subject to a terminal disclaimer.

(21) Appl. No.: 13/448,530

(22) Filed: Apr. 17, 2012

(65) Prior Publication Data

US 2012/0203306 A1   Aug. 9, 2012

Related U.S. Application Data

(63) Continuation-in-part of application No. 13/028,301, filed on Feb. 16, 2011, which is a continuation-in-part of application No. 12/766,383, filed on Apr. 23, 2010, now Pat. No. 7,985,184, which is a continuation-in-part of application No. 11/223,259, filed on Sep. 10, 2005, now Pat. No. 7,713,200.

(51) Int. Cl.
*A61N 1/36* (2006.01)
*A61N 1/372* (2006.01)

(52) U.S. Cl.
CPC ........ *A61N 1/37217* (2013.01); *A61N 1/37252* (2013.01)
USPC .......................................................... 607/60

(58) Field of Classification Search
USPC ......................................... 607/2, 32, 60, 437
See application file for complete search history.

(56) References Cited

U.S. PATENT DOCUMENTS

| 5,092,336 A | 3/1992 | Fink |
| 6,140,740 A | 10/2000 | Porat |
| 6,198,965 B1 | 3/2001 | Penner |
| 6,237,398 B1 | 5/2001 | Porat |
| 6,239,724 B1 | 5/2001 | Doron |
| 6,277,078 B1 | 8/2001 | Porat |
| 6,416,474 B1 | 7/2002 | Penner |
| 6,431,175 B1 | 8/2002 | Penner |

(Continued)

FOREIGN PATENT DOCUMENTS

EP  1449564  8/2004

OTHER PUBLICATIONS

Choy BY et al. Formation of Desired Waveform and Focus Structure by Time Reversal Acoustic Focusing System. 2006 IEEE Ultrasonics Symposium, pp. 2177-2181.

(Continued)

*Primary Examiner* — Christopher Koharski
*Assistant Examiner* — Jeremiah Kimball
(74) *Attorney, Agent, or Firm* — Boris Leschinsky

(57) ABSTRACT

A time-reversal acoustics system includes a transmitter configured to send a high intensity acoustic waveform signal focused on an implantable receiver. The receiver includes a piezoelectric transducer configured to convert received acoustic energy to an electrical signal used to energize an internal electrical circuit. Such circuit may be used to operate at least one tissue stimulating electrode, at least one sensor such as an ECG sensor, charge an internal battery or perform another useful function. The system of the invention may be used as a wireless cardiac pacemaker or a neurostimulator.

13 Claims, 4 Drawing Sheets

(56) References Cited

U.S. PATENT DOCUMENTS

| | | |
|---|---|---|
| 6,432,050 B1 | 8/2002 | Porat |
| 6,475,170 B1 | 11/2002 | Doron |
| 6,486,588 B2 | 11/2002 | Doron |
| 6,490,469 B2 * | 12/2002 | Candy .................. 600/407 |
| 6,504,286 B1 | 1/2003 | Porat |
| 6,622,049 B2 | 9/2003 | Penner |
| 6,628,989 B1 | 9/2003 | Penner |
| 6,699,186 B1 | 3/2004 | Wolinsky |
| 6,720,709 B2 | 4/2004 | Porat |
| 6,743,173 B2 | 6/2004 | Penner |
| 6,764,446 B2 | 7/2004 | Wolinsky |
| 6,840,956 B1 | 1/2005 | Wolinsky |
| 7,006,864 B2 | 2/2006 | Echt |
| 7,024,248 B2 | 4/2006 | Penner |
| 7,050,849 B2 | 5/2006 | Echt |
| 7,184,830 B2 | 2/2007 | Echt |
| 7,198,603 B2 | 4/2007 | Penner |
| 7,201,749 B2 | 4/2007 | Govari |
| 7,273,457 B2 | 9/2007 | Penner |
| 7,283,874 B2 | 10/2007 | Penner |
| 7,489,967 B2 * | 2/2009 | Von Arx et al. ............. 607/32 |
| 7,522,962 B1 | 4/2009 | Doron |
| 7,558,631 B2 | 7/2009 | Cowan |
| 7,572,228 B2 | 8/2009 | Wolinsky |
| 7,580,750 B2 | 8/2009 | Doron |
| 7,587,291 B1 | 9/2009 | Sarvazyan |
| 7,606,621 B2 | 10/2009 | Brisken |
| 7,610,092 B2 | 10/2009 | Cowan |
| 7,617,001 B2 | 11/2009 | Penner |
| 7,621,905 B2 | 11/2009 | Penner |
| 7,641,619 B2 | 1/2010 | Penner |
| 7,702,392 B2 | 4/2010 | Echt |
| 7,713,200 B1 * | 5/2010 | Sarvazyan et al. ........... 600/437 |
| 7,751,881 B2 | 7/2010 | Cowan |
| 7,765,001 B2 | 7/2010 | Echt |
| 7,809,438 B2 | 10/2010 | Echt |
| 7,813,808 B1 | 10/2010 | Doron |
| 7,848,815 B2 | 12/2010 | Brisken |
| 7,890,173 B2 | 2/2011 | Brisken |
| 7,894,904 B2 | 2/2011 | Cowan |
| 7,894,907 B2 | 2/2011 | Cowan |
| 7,894,910 B2 | 2/2011 | Cowan |
| 7,899,541 B2 | 3/2011 | Cowan |
| 7,899,542 B2 | 3/2011 | Cowan |
| 7,930,031 B2 | 4/2011 | Penner |
| RE42,378 E | 5/2011 | Wolinsky |
| 7,948,148 B2 | 5/2011 | Porat |
| 7,953,493 B2 | 5/2011 | Fowler |
| 7,996,087 B2 | 8/2011 | Cowan |
| 8,078,278 B2 | 12/2011 | Penner |
| 8,078,283 B2 | 12/2011 | Cowan |
| 2002/0077673 A1 | 6/2002 | Penner |
| 2002/0188323 A1 | 12/2002 | Penner |
| 2003/0005770 A1 * | 1/2003 | Berryman ............... 73/602 |
| 2004/0044393 A1 | 3/2004 | Yarden |
| 2004/0077937 A1 | 4/2004 | Yarden |
| 2004/0162507 A1 * | 8/2004 | Govari ................ 601/2 |
| 2004/0162550 A1 * | 8/2004 | Govari et al. ............. 606/27 |
| 2004/0172083 A1 * | 9/2004 | Penner ................. 607/35 |
| 2005/0070962 A1 | 3/2005 | Echt |
| 2006/0161061 A1 | 7/2006 | Echt |
| 2006/0241523 A1 | 10/2006 | Sinelnikov |
| 2007/0027508 A1 | 2/2007 | Cowan |
| 2007/0129637 A1 | 6/2007 | Wolinsky |
| 2007/0274565 A1 | 11/2007 | Penner |
| 2008/0077440 A1 | 3/2008 | Doron |
| 2008/0103553 A1 | 5/2008 | Penner |
| 2008/0191581 A9 | 8/2008 | Penner |
| 2008/0294208 A1 | 11/2008 | Willis |
| 2009/0216128 A1 | 8/2009 | Sarvazyan |
| 2009/0270742 A1 | 10/2009 | Wolinsky |
| 2009/0270790 A1 | 10/2009 | Raghavan |
| 2010/0004718 A1 | 1/2010 | Doron |
| 2010/0016911 A1 | 1/2010 | Willis |
| 2010/0228308 A1 * | 9/2010 | Cowan et al. ............ 607/14 |
| 2010/0234924 A1 | 9/2010 | Willis |
| 2010/0286744 A1 | 11/2010 | Echt |
| 2011/0112600 A1 | 5/2011 | Cowan |
| 2011/0118810 A1 | 5/2011 | Cowan |
| 2011/0144720 A1 | 6/2011 | Cowan |
| 2011/0166620 A1 | 7/2011 | Cowan |
| 2011/0166621 A1 | 7/2011 | Cowan |
| 2011/0237967 A1 | 9/2011 | Moore |

OTHER PUBLICATIONS

Sarvazyan A et al. Time-Reversal Acoustic Focusing System as a Virtual Random Phased Array. IEEE Transactions on Ultrasonics, Ferroelctrics, and Frequency Control, vol. 57, No. 4, pp. 812-817, 2010.

Sarvazyan A et al. A Comparative Study of Systems Used for Dynamic Focusing of Ultrasound. Acoustical Physics, vol. 55, No. 4-5, pp. 630-637, 2009.

Zaraska W, Thor P, Lipinski M et al. Design and Fabrication of Neurostimulator implants—selected problems. Microelectronics reliability 45;1930-1934, 2005.

* cited by examiner

SYSTEMS FOR REMOTE GENERATION OF ELECTRICAL SIGNAL IN TISSUE BASED ON TIME-REVERSAL ACOUSTICS

CROSS-REFERENCE DATA

This patent application is a continuation-in-part of a co-pending U.S. patent application Ser. No. 13/028,301 filed 16 Feb. 2011 entitled "ULTRASOUND DIAGNOSTIC AND THERAPEUTIC DEVICES"; which is in turn a continuation-in-part of a U.S. patent application Ser. No. 12/766,383 filed 23 Apr. 2010 entitled "Ultrasound-assisted drug-delivery method and system based on time reversal acoustics", now U.S. Pat. No. 7,985,184; which in turn is a continuation-in-part of U.S. patent application Ser. No. 11/223,259 filed 10 Sep. 2005 entitled "Wireless beacon for time-reversal acoustics, method of use and instrument containing thereof", now U.S. Pat. No. 7,713,200. All of the above mentioned patent documents are incorporated herein by reference in their respective entireties.

BACKGROUND OF THE INVENTION

The present invention relates generally to Time-Reversal Acoustics (TRA) systems used to focus acoustic waves for various useful applications in the biomedical area. More particularly, the systems of the invention include an acoustic transmitter and an implanted or percutaneously inserted acoustic receiver. The receiver is configured to generate a useful electrical signal in response to receiving an acoustical signal from the transmitter. In addition, the receiver is configured to emit an electromagnetic wave (also referred to as radiofrequency or RF) signal to the transmitter. Such electromagnetic wave signal may be used as a feedback signal for tuning time-reversal acoustic system to focus acoustic waves at the location of such receiver as well as to transmit other pertinent information back to the transmitter. The system may be used for various useful purposes, such as cardiac pacing, neurostimulation or charging a battery of an implant system including the receiver. The device and method of the invention may be used advantageously as part of a medical instrument inside a patient's body as well as for other applications described below in more detail.

For the purposes of this description, the term "patient" is used to describe any person, animal, or other living being in which the medical instrument is inserted temporarily or implanted on a permanent basis. The term "medical instrument" or just "instrument" is used to describe various medical inserts and implants such as but not limited to needles, various scopes of flexible or rigid nature, implants, stents including drug-eluting stents, pacemakers and parts thereof, implantable electrical stimulators of all kinds including neurostimulators, neuromodulation devices, vagus nerve stimulators, hypoglossal nerve stimulators, thalamus stimulators, sacral nerve stimulators and spinal cord stimulators, implantable hearing aid devices including inner ear microtransmitters, cannulas, balloons, probes, guidewires, trocars, sensors, markers, infusion pumps, various implants functioning from an internal battery, and local medication delivery devices.

Electrical stimulation of nerves, nerve roots, and/or other nerve bundles for the purpose of treating patients has been known and actively practiced for many decades. Application of an electrical field between electrodes to stimulate nerve tissues is known to effectively modify signal pathways both with unidirectional and bidirectional stimulation along the nervous system to signal the brain or to signal organs to alleviate symptoms or control function. These applications are currently practiced with both externally applied devices and implanted devices. For example, applying specific electrical pulses to nerve tissue or to peripheral nerve fibers that corresponds to regions of the body afflicted with chronic pain can induce paresthesia, or a subjective sensation of numbness or tingling, or can in effect block pain transmission to the brain from the pain-afflicted regions. Many other examples include electrical stimulation of various branches of the vagus nerve bundle for control of heart rate, mediating hypertension, treating congestive heart failure, controlling movement disorders, tremors, treating obesity, treating migraine headache, and effecting the urinary, gastrointestinal, and/or other pelvic structure in order to treat urgency frequency, urinary incontinence, and/or fecal incontinence. Still other branches of the vagus nerve have been used to treat neuropsychiatric disorders. Additionally, applications are also known for electrical stimulation of nerves and nerve bundles in many other specific, selected nerve regions: for example, the pudendal or sacral nerves for controlling the lower urinary tract.

Neurostimulation may also be useful in treating a variety of other diseases including depression, paralysis, sleep apnea, angina, digestive tract disorders, Alzheimer's, obsessive-compulsive disorder, Parkinson's, epilepsy, accelerated healing of strains and tears, bone regrowth/repair in fractures, pain-pumps for intrathecal baclofen administration for spasticity, pain-pumps for intrathecal opioid administration for chronic neuropathic pain syndromes, spinal cord stimulators for failed back syndrome and cancer-related pain, neuropathic pain syndromes (e.g., herpetic neuralgia, phantom-limb pain—especially for blast/rocket victims), traumatic brain injury, and many others.

Depending on the individual patient, direct nerve stimulation can effectively modify signal pathways along the nerve, to and from the brain, and to and from organs in the body and thus provide relief of symptoms or control of bodily function. Treatment regimens and targeted nerve locations are known in related art through use of current, common stimulation devices and methods. Commonly implanted devices for nerve stimulation are made by such companies as Cyberonics, Medtronic, Advanced Bionics, and others.

Devices to provide such electrical stimulation may in some cases be applied externally, or in other cases it is more advantageous to implant or percutaneously insert all or part of the device. This invention pertains to devices and systems in which at least one portion providing direct electrical stimulation to the body tissue is either permanently or temporarily implanted or inserted. Such devices may include pacemakers, implantable defibrillators, neurostimulators and other devices for stimulating cardiac and other tissues.

Electrical energy sources connected to electrode/lead wire systems have typically been used to stimulate tissue within the body. The use of lead wires is associated with significant problems such as complications due to infection, lead failure, and electrode/lead dislodgement. The use of leads to accomplish tissue stimulation also limits the number of accessible locations in the body, as well as the ability to stimulate tissue at multiple sites (multisite stimulation). For instance, the treatment of epilepsy may require a minimum of perhaps 5 or 6 stimulation sites. Other diseases, such as Parkinson's disease, may benefit from more stimulation sites than the two utilized in current systems.

Beyond the problems of outright failure and placement difficulties, present day pacemaker leads inherently cause problems for pacemaker systems by acting as antennae, coupling electromagnetic interference (EMI) into the pacemaker electronics. Particularly problematic is interference with cardiac electrogram sensing and signal processing circuitry.

With the exponential rise in the number of cellular telephones, wireless computer networks, and the like, pacemaker lead induced EMI will continue to spur increased complexity in the design of, and require significant testing of pacemaker devices.

Prior art describes various systems and methods for using acoustic energy to wirelessly energize an implanted component in order to generate a useful electrical signal inside the body of a patient. Examples of such systems may be found in the following US Patents and US Patent Applications, which are incorporated herein by reference in their entireties:

| | | | | | |
|---|---|---|---|---|---|
| 6,475,170 | 7,050,849 | 7,621,905 | 7,899,541 | US20020077673 | US20080294208 |
| 6,486,588 | 7,184,830 | 7,641,619 | 7,899,542 | US20020188323 | US20090270742 |
| 6,504,286 | 7,198,603 | 7,702,392 | 7,930,031 | US20040044393 | US20100004718 |
| 6,622,049 | 7,273,457 | 7,751,881 | 7,948,148 | US20040077937 | US20100016911 |
| 6,628,989 | 7,283,874 | 7,765,001 | 7,953,493 | US20050070962 | US20100228308 |
| 6,699,186 | 7,522,962 | 7,809,438 | 7,996,087 | US20060161061 | US20100234924 |
| 6,720,709 | 7,558,631 | 7,813,808 | 8,078,278 | US20070027508 | US20100286744 |
| 6,743,173 | 7,572,228 | 7,848,815 | 8,078,283 | US20070129637 | US20110112600 |
| 6,764,446 | 7,580,750 | 7,890,173 | RE42378 | US20070274565 | US20110118810 |
| 6,840,956 | 7,606,621 | 7,894,904 | | US20080077440 | US20110144720 |
| 7,006,864 | 7,610,092 | 7,894,907 | | US20080103553 | US20110166620 |
| 7,024,248 | 7,617,001 | 7,894,910 | | US20080191581 | US20110166621 |
| | | | | | US20110237967 |

Prior art devices typically include an acoustic transmitter and an acoustic receiver. The transmitter may be located inside or outside the body and the receiver is a small implantable or inserted component placed at or near the internal organ or tissue, which can benefit from direct electrical stimulation or another application of a useful electrical signal. The electrical signal is typically generated by the receiver using the acoustic energy received from the transmitter.

A key limitation of this arrangement is that the acoustic energy is unfocused and therefore is mostly dissipated in the surrounding tissues. Only a small portion of the acoustic energy is used for the purpose of generating a useful electrical signal. Because of that, the system has to be configured to rely only on small electrical energy available from the receiver or to transmit excessive acoustic energy which may jeopardize surrounding tissues.

Some systems of the prior art have suggested using phased array ultrasound transducers as part of an acoustic transmitter in order to focus ultrasound energy at the receiver location. This approach is of course better than any unfocused energy transmission but it too has a number of important limitations:
  Location of the receiver has to be known in advance, which may not be easy to obtain;
  Receiver has to remain in the same location, which is difficult to control due to breathing and other natural tissue movements;
  A large number of individual transducers in the array is needed for effective focusing of ultrasound making the device complicated, large, and expensive;
  Accurate predictive modeling of ultrasound waves passing through various types of soft tissues and bones is needed for the system to work effectively so that signals from all transducers converge on a single point where the receiver is located. Shifting tissues and inaccuracy of modeling make focusing less reliable.

Focusing of ultrasonic waves using a concept of Time-Reversed Acoustics (TRA) provides an elegant possibility of both temporal and spatial concentrating of acoustic energy in highly inhomogeneous media. It was initially developed by M. Fink of the University of Paris. The TRA technique is based on the reciprocity of acoustic propagation, which implies that the time-reversed version of an incident pressure field naturally refocuses on its source. The general concept of TRA is described in a seminal article by Fink, entitled "Time-reversed acoustics," Scientific American, November 1999, pp. 91-97, which is incorporated herein by reference. U.S. Pat. No. 5,092,336 to Fink, which is also incorporated herein by reference, describes a device for localization and focusing of acoustic waves in tissues.

An important issue in the TRA method of focusing acoustic energy is related to obtaining initial signal from the target area. It is necessary to have a beacon located at the desired tissue location to record and provide an initial signal from the focal region. In the TRA systems described in the prior art, most commonly used beacon is a hydrophone placed at the chosen target point. Other disclosed beacons may include highly reflective targets that provide an acoustical feedback signal for TRA focusing of acoustic beam. The need to have a beacon in the target region limits the applications of TRA focusing methods.

While scattering and numerous reflections from boundaries are known to greatly limit and even completely diminish conventional ultrasound focusing, in TRA they lead to the improvement of the focusing results. Fink et al. have demonstrated a remarkable robustness of TRA focusing: the more complex the medium, the sharper the focus.

The advantages of the TRA-based focusing systems over conventional ultrasound focusing are numerous:
  TRA focusing approach is capable to precisely deliver ultrasound energy to the chosen region regardless of the heterogeneity of the propagation medium, for example behind the ribs or inside the skull. The ability to effectively localize ultrasound energy and avoid exposure of surrounding tissues to high levels of acoustic energy passing therethrough is important in many medical applications including ultrasound surgery and ultrasound-enhanced drug delivery;
  TRA focusing systems may produce more effective spatial concentration of ultrasound energy than traditional systems; the focus volume can approach ultrasound diffraction limit, it can have a shape of a sphere rather than an elongated ellipsoid typically formed by most traditional focusing systems;
  TRA focusing system may produce pulses with arbitrary waveforms in a wide frequency band. Ability to generate various waveforms is important in many applications, for example for optimizing the outcome of the ultrasound-enhanced drug delivery where the main mechanism of ultrasound action, sonoporation, is related to cavitation; the threshold of cavitation depends strongly on frequency and the form of the applied signal.

Several examples of TRA focusing systems employing a passive ultrasound reflector or an active ultrasound emitter as a TRA receiver are described in the U.S. patent application Ser. No. 10/370,134 (US Patent Application Publication No. 2004/0162550) and U.S. patent application Ser. No. 10/370,381 (US Patent Application Publication No. 2004/0162507) to Govari et al. as well as a European Patent Application No. EP1449564, all of which are incorporated herein by reference. Described in these patent documents is a TRA-based high intensity ultrasound system designed for isolation of pulmonary veins. The receivers are implanted piesotransducers designed to reflect or emit ultrasound signal to be detected by an array of external transducers. In case of an active beacon, the electrical energy is typically delivered thereto via electrical leads from the control unit. The electrical energy is converted by the active beacon into the acoustic energy and transmitted to the outside of the body where it is picked up by outside sensors to determine the exact location of the receiver. In some cases, wireless circuitry and method of energy transmission is used to transmit the electrical energy to the active beacon, where it is then converted to the acoustic energy and emitted by the receiver. Alternatively, the receiver may comprise a passive ultrasound reflector, such as the one having certain geometry to produce a sharp and easily distinguishable ultrasound signature.

The need exists for an acoustically-powered system capable of delivering electrical energy to power an implantable electrical circuit. Such circuit may then be used as a leadless implantable tissue stimulation electrode, physiological sensor or a charger for an implantable battery.

SUMMARY OF THE INVENTION

Accordingly, it is an object of the present invention to overcome these and other drawbacks of the prior art by providing a novel TRA-based system configured to deliver electrical energy to energize an internal electrical circuit.

It is another object of the present invention is to provide a novel TRA-based system configured to wirelessly energize at least one tissue stimulation electrode, such as for cardiac pacing or neurostimulation purposes.

It is yet a further object of the present invention to provide a wireless acoustic system capable of frequently updating the TRA signal to seamlessly focusing high intensity acoustic wave signal on an implantable receiver even in circumstances of this receiver moving inside the body.

The present invention provides acoustically-based methods and devices to energize a useful internal electrical circuit—for example to activate an electrode in order to stimulate a cardiac muscle, nerves or other body tissues utilizing acoustic energy. The system mainly includes a transmitter and a receiver. The transmitter of the system may be configured to emit appropriately formed acoustic signal towards the receiver. The receiver includes a piezoelectric receiving transducer configured to receive the acoustic energy and convert it into electrical energy. In its most basic form, the receiving transducer is made for example of piezopolymer or piezoceramic material. The receiver may be configured to apply that electrical energy to a useful purpose such as activating internal stimulating electrodes or charge a battery of an implanted device.

The present invention encompasses a method of TRA focusing with remote feedback from one or more focal points in the form of electromagnetic waves generated by one or more miniature receiving piezoelectric transducers incorporated into receivers placed in the target areas and affected by the initial acoustic wave. Once the initial acoustic wave transmission causes energizing of such receiving piezoelectric transducer, it generates an electromagnetic wave feedback signal reproducing exactly the waveform of the received acoustic wave, which is then emitted via an optionally integrated internal radiofrequency emitting antenna. Such electromagnetic wave signal can be used by transmitter to "home-in" the acoustic waves on the receiver using Time-Reversal Acoustics principles.

The receiver may also be configured to send out an electromagnetic wave signal with other useful information such as data from internal sensors. The receiver may be implanted at a location where it is desired to provide electrical stimulation, with stimulating electrodes in direct contact with the cardiac or other body tissue. Optionally, two or more receivers may be implanted to be controlled by a single transmitter or several transmitters. Each of these multiple receivers may be configured to operate one or several electrodes and may include one or more sensors.

In embodiments, a cardiac pacemaker or a neurostimulator employing ultrasonic energy transfer according to the present invention may include a receiver configured to be implanted to any desired tissue or location in the body. Various minimally invasive, transvascular techniques and tools (e.g. stylets, cannulas, etc.) may be adapted and used to deliver, place, embed, wrap about, and secure the receiver to these locations. The receiver may additionally be adapted to provide permanent attachment to the implant site including using helical coils, barbs, staples, clips, sutures or the like. Chronic endothelialization may be encouraged by receiver design features such as tines or irregularities in its outer surface, or by bonding onto the outer surface of materials which are known to stimulate cellular growth and adhesion.

Functionally, the receiver may include 1) a piezoelectric receiving transducer to receive the acoustic energy from the transmitter and transform it into electrical energy, 2) an internal electrical circuit to transform received electrical impulse into an electrical waveform having desired characteristics, as well as optionally 3) one or more stimulating electrodes to transfer the electrical energy to the stimulation site, 4) one or more implanted sensors, and 5) an additional electrical circuit to form and send an electromagnetic wave signal.

The receiver may generate a predetermined electrical signal using acoustic energy from the transmitter. Alternatively, the receiver may use information extracted from the acoustic wave signal transmission itself to configure the electrical output signal, for example the pulse width of the transmission may determine the pulse duration/width of the electrical output signal. Additionally, the receiver may comprise circuitry for additional control logic, for example selecting activation of individual receivers (on-off control), timing delays, waveform shape adjustments, or the like. In particular, when more than one receiver are implanted and controlled by a single transmitter, the transmitted energy signal may contain addressing or selection information identifying which receiver is to be activated at any particular time.

In embodiments, the transmitter may be placed over the skin or implanted subcutaneously utilizing known surgical techniques, including locations near the desired stimulation site. The transmitter and the receiver may include some, or most, or all elements of currently available neurostimulators or cardiac pacemakers, with specific adaptations pertinent to this invention. These typical pacemaker elements may include a power source, pacemaker control and timing circuitry, a sensing system, signal conditioning and analysis circuitry for the various electrodes and detectors, and a system for communication between the receiver and the transmitter and optionally an outside control console.

The sensing system may include one or more of the following sensors: an ECG or other electrical activity sensor; a motion detector; a local, core body or other temperature sensor; a pressure sensor; an impedance sensor; a sensor to indicate rejection of a transplanted organ; a heart rhythm sensor; a force sensor; a chemical substance detector; and a sensor indicating remaining electrical charge level for an internal battery. In embodiments, external sensors may also be deployed as part of the system—both attached directly to the patient and sensors monitoring the patient from a distance.

Data transmission between the transmitter and the console may include on/off signals, tuning and adjustment signals, as well as various other diagnostic and programming information. It may be wirelessly transmitted using for example a second radiofrequency link, in addition to a radiofrequency link between the receiver and a transmitter.

The transmitter contains TRA electronic unit coupled via an ultrasound amplifier to an acoustic emitting transducer to generate high intensity acoustic energy and transmit it in the general direction of the implanted receiver. The duration, timing, and power of the acoustic energy transmission may be preprogrammed or controlled as required, for example in response to detected natural or induced physiological events or conditions, and per known electrophysiological parameters, by the appropriate control electronics.

A single receiver may be implanted as described above for a single site stimulation; additionally it may be possible to implant a plurality of receivers which may stimulate the desired tissue either simultaneously by receiving the same transmitted acoustic energy, or sequentially through fixed or adjustable delays after receiving the same transmitted acoustic energy, or independently by responding only to TRA-specific signal information of the transmitted acoustic energy of a specific character (i.e., of a certain frequency, amplitude, or by other modulation or encoding of the acoustic waveform) intended to energize only that specific receiver.

In embodiments, the system of the invention may be configured to function as a wireless stand alone single chamber pacemaker implanted into or attached to the right atrium of the heart in order to provide right atrial pacing, or implanted into or attached to either the right ventricle or left ventricle of the heart in order to provide right or left ventricular pacing. The transmitter may incorporate most or all of the features of a contemporary single chamber pacemaker device, typically known to be used for an AAI (atrial) or VVI (ventricular) mode pacing. Such conventional pacemakers commonly utilize right atrial or right ventricular leads for treatment of bradyarrhythmias, or slow heart rate. A pacemaker system of the invention may advantageously not require the use of electrical leads of any kind. Moreover, the ability to use a left ventricular lead alone enables the potential hemodynamic benefit of left ventricular pacing compared to a right ventricular pacing without the use of electrical leads of any kind. Further enhancement to this single chamber pacemaker system may include other patient physiological sensor(s) that adjust the patient's paced rate in response to the sensor, e.g., motion detectors. This may provide the capability for AAIR and VVIR modes of pacing.

As described previously, sensing of electrical activity in the body and other patient physiological information such as movement, temperature, blood pressure, intracavity impedance changes, or heart sounds may be provided from electrodes and/or other sensors incorporated onto or into or within the housing of, or connected to the implanted transmitter or receiver. In embodiments, an accelerometer may be used as a sensor for mechanical/motion sensing or for heart sounds sensing. Examples for anticipated electrical activity sensing include monitoring of intrinsic cardiac beats, pacemaker pacing artifacts, non-intrinsic cardiac beats initiated by pacemaker pacing outputs, and the like.

In embodiments, the system of the invention may be constructed to function as a dual chamber pacemaker with operation similar to contemporary dual chamber (DDD) pacemakers. Such a pacemaker may be realized by utilizing two implantable receivers and either one or two implantable transmitters. One receiver may be implanted into the right atrium as described above; the second receiver may be implanted into the right or left ventricle. One transmitter may be configured to transmit ultrasound energy to the two implanted receivers, causing them to provide pacing stimulation to the atrium and ventricle either simultaneously or sequentially. If sequential, timed stimulation to the atrium and ventricle is required, various means to accomplish this may be incorporated into the wireless pacemaker system. In one possibility, a single acoustic waveform may be transmitted at the time necessary to activate the first, typically atrial, receiver. The second, typically ventricular, receiver may be of a modified design incorporating circuitry and devices to capture and temporarily store the acoustic energy transmitted at the time of atrial stimulation, and after a fixed delay provide this energy to its stimulation electrodes to pace the ventricle. Sequential stimulation may also be accomplished under direct control of the transmitter, possibly utilizing the sequential transmission of acoustic energy at different frequencies, with each receiver tuned to respond only to a specific acoustic signal. Other methods including amplitude modulation, frequency modulation, time-division modulation, or other modulation or encoding of the acoustic waveform may also permit selective and sequential pacing from multiple implanted receivers. Alternately, two transmitters may be deployed, each configured to transmit acoustic energy only to one specific receiver, such configuration achieved either through spatial separation, frequency separation, or other modulation or encoding means as previously described.

In such a dual chamber system, sensing of the electrogram or other patient physiological information may be provided from electrodes and/or other sensors incorporated onto or into or within the housing of the implanted transmitter. Further enhancement to this dual chamber pacemaker system may include other patient physiological sensor(s) that adjust the patient's paced rate in response to the sensor, e.g., motion detectors. This may provide the capability for DDDR modes of pacing in which a pacemaker mode in which the device paces and senses both chambers of the heart and is capable of adjusting the pacing rate automatically.

The wireless system of the invention may also be configured to function as a standalone antitachycardia pacemaker. In this embodiment of the invention, one or more receivers may be implanted at one or more cardiac sites, and the transmitter may be either a subcutaneously implanted device or an externally applied device.

In further aspects of the present invention, the transmitter may be implanted at a remote tissue location within or external to the body. The receiver may be either permanently implanted or temporarily placed at a target location with stimulating electrodes in direct contact with the body tissue to be stimulated. By observing changes in a patient response and/or device measurement in response to different combinations of remote and target tissue locations, the sites chosen for permanent implantation may be optimized and selected. Patient response(s) may be any quantitative or qualitative physiologic responses to the stimulation, typically being associated with the desired beneficial response. Device measurement(s) may be signal strength, transmission efficiency, or the like. Applications for such optimized placement methods may include applying electrical stimulation for the treatment of peripheral muscle strains and tears, bone fractures, musculoskeletal inflammation, chronic pain, Parkinson's disease, epileptic seizures, high blood pressure, cardiac arrhythmias, heart failure, coma, stroke, hearing loss, dementia, depression, migraine headaches, sleep disorders, gastric motility disorders, urinary disorders, obesity, and diabetes.

The present invention may be used for remotely charging internal batteries of the devices implanted in soft biological tissue or another inaccessible object. Remote recharging of batteries of internal implants, such as urinary tract control devices, cardiac pacemakers, cochlea implants and deep brain neurostimulators among others is an important problem to which there is currently no adequate solution. Recharging of an implant battery in a noninvasive manner may allow avoiding a second operation of replacing the originally placed device.

Additional advantageous use of the system of the invention may include energizing on demand of an otherwise dormant electrically-powered device.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

Figure 1:
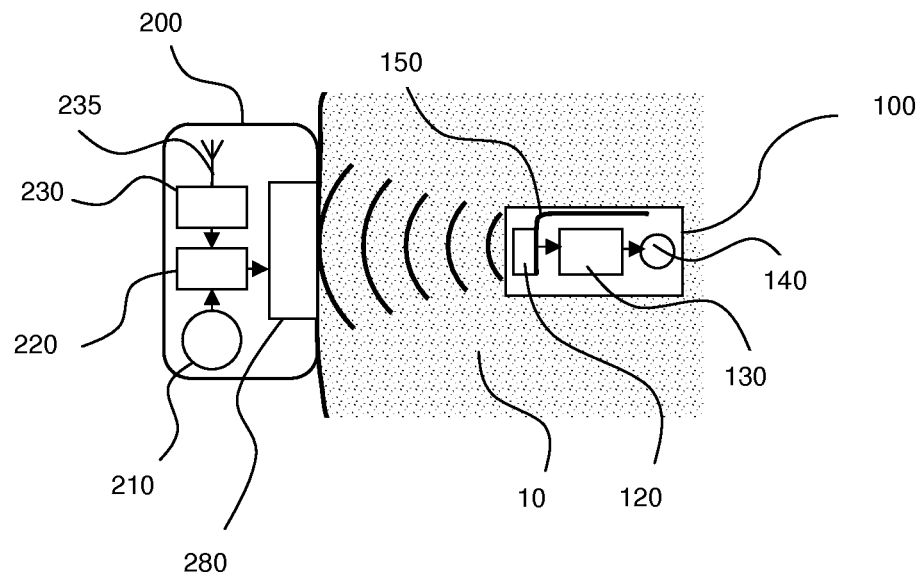
FIG. 1 is a general schematic depiction of the system including an external transmitter and an implanted receiver.

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure. A detailed description of the present invention follows with reference to accompanying drawings in which like elements are indicated by like reference letters and numerals.

The invention comprises in general an ultrasound transmitter configured to deliver acoustic energy and information to one or more implantable receivers configured for conversion of the acoustic energy into electrical energy of a form that can be used for example to electrically stimulate the target tissue. Acoustic energy may be emitted as a single burst or multiple bursts with appropriate selection of the following parameters:

| Parameter | Value Range |
|---|---|
| Ultrasound frequency | 20 kHz-10 MHz |
| Burst Length (#cycles) | 1-1,000 |
| Stimulation Pulse Duration | 0.1 µS-10 mS |
| Duty Cycle | 0-100% |
| Mechanical Index | ≤1.9 |

The transmitter of the invention may contain an acoustic emitting transducer or transducers of appropriate sizes and configurations to generate sufficient acoustic power and signal information to achieve the desired electrical stimulation at the location of an implanted receiver. It may also include a reverberation chamber as described below. Additionally, multiple implanted receivers may be placed within the region sonicated by the transmitter. A wider system of the invention may include additional electrodes and/or various sensors used for automatic adjustments and self-control by the system. Multiple receivers may function simultaneously, however it is possible for multiple devices to function independently as described above. Such a wireless stimulator comprising a transmitter and at least one receiver may preferably operate at an ultrasound frequency between 20 kHz and 10 MHz, and more preferably operate at a frequency between 100 kHz and 1 MHz.

The acoustic waveform generated by the transmitter may carry pulse width and pulse amplitude information used by the receiver to construct a corresponding electrical output. Alternatively, the signal information may comprise address information (identifying a particular receiver or group of devices to trigger), triggering information to initiate output (turn on or off) the receiver(s), delay information to control when the receiver (s) initiate output, the level or other characteristics of the electrical power to be delivered, and the like. The receiver(s) may have circuitry to permit decoding of the signal information (which may be encoded in the power transmission), and additional circuitry such as a digital gate which can turn on and off the electrical output, timer circuitry to permit a delay in turning on or off the electrical output, and the like.

The transmitter may typically include sensors such as electrodes for detecting the patient's electrogram and/or pacing signals (pacing artifacts) from other devices, and in certain embodiments additional physiological sensors as described above. Circuitry and algorithms for utilizing these signals for control of the stimulating function may be provided. Such electrodes and other sensors may be preferably disposed on or incorporated into or within the housing of either the receiver or the transmitter.

FIG. 1 shows a schematic diagram of one system of the invention. It shows the external transmitter 200 and the implanted receiver 100 located inside a patient's tissue 10.

The receiver 100 contains a piezoelectric receiving transducer 120, which converts transmitted acoustic energy it into an electrical signal. This electrical signal is applied to energize an internal electrical circuit 130, the input of which is operably coupled with the receiving transducer 120. The internal electrical circuit 130 may be a battery charger and/or a signal conditioner and which may have one of many known circuit configurations, producing an appropriate voltage pulse. This electrical signal may be applied then to one or more tissue stimulating electrodes 140 operably coupled to the output of the internal electrical circuit 130. Such electrodes may be incorporated onto the outer surface of the receiver 100, and thus be in direct contact with the tissue 10 which is to be stimulated. The receiver 100 includes an emitting antenna 150 operably coupled with the receiving transducer 120 to transmit an electromagnetic wave signal.

Figure 2:
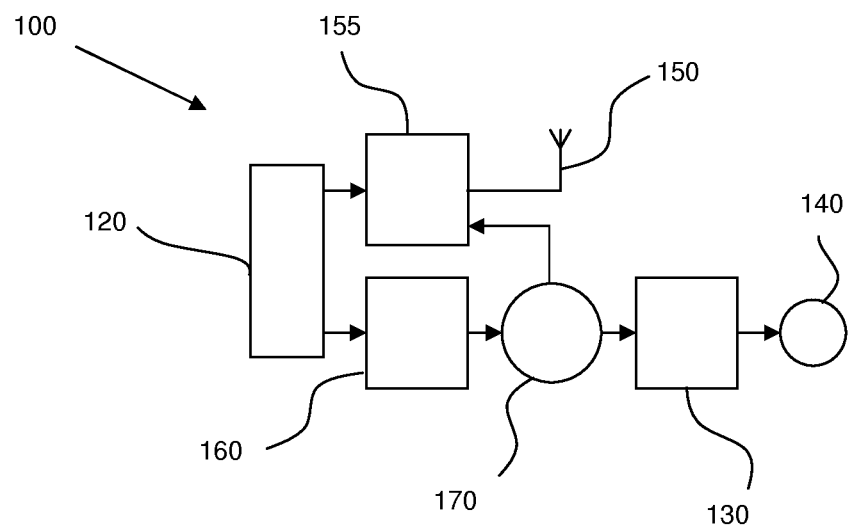
FIG. 2 shows a general block-diagram of implanted battery-powered receiver with a stimulating electrode.

Additional details of a receiver 100 are shown in FIG. 2 and may include an RF amplifier 155 configured to amplify the electromagnetic signal before emitting it by the antenna 150. The receiver 100 may also include a charger 160 and a battery 170 configured to energize operation of the electrode 140. In this case, acoustic energy from the transmitter 200 may be used to periodically recharge the battery 170, which is then used for intermittent or continuous powering of the electrode 140 for the purposes of electrical stimulation of desired tissue or organ.

The piezoelectric receiving transducer 120 and its electronic circuit may be enclosed within a hermetically sealed housing made of a biologically compatible material such as for example stainless steel or titanium. Such housing may be constructed to be electrically insulating but acoustically transparent. Its circuit assembly may be fabricated using known surface-mount or hybrid assembly techniques, upon either a fiberglass or ceramic substrate. Stimulating electrodes may be fabricated of material commonly used in implanted electrodes, such as platinum or platinum-iridium design. Necessary electrical functional connections between the receiving transducer 120, internal electrical circuit 130, and electrodes 140 are shown in the drawings. The receiver 100 of this design may also incorporate means such as helical coils, barbs, tines, clips, and the like (not shown) to affix the device within, or attach or wrap it onto, or place it in direct contact with the nerve or tissue at the desired location. Such fixation elements may vary depending on the intended implant location and delivery method. Typical dimensions of receiver 100 may be 1.5 cm in length by 3 mm in diameter, and preferably less than 1.0 cm in length by 2 mm in diameter, exclusive of fixation elements.

The transmitter 200 may include:
- a battery 210 or other source of electrical energy such as using an AC outlet for external version thereof,
- a TRA electronic unit 220 configured to receive, time-reverse, and amplify the radiofrequency feedback signal; the TRA unit may also include a control and timing module, which stores setup parameters and uses this information in conjunction with the acquired TRA feedback signal to generate the required initial and driving signals for the ultrasound amplifier, which in turn applies electrical energy to the ultrasound emitting transducer 280,
- an emitting transducer 280 to produce the desired initial and then focused acoustic waveform, and
- an RF receiver 230 with a receiving RF antenna 235, all assembled within an appropriate housing. Connections of inputs and outputs of respective components are shown in the figures.

External configuration of a transmitter 200 may be especially advantageous for "on demand" applications of electrical stimulation or energizing an internal electrical circuit from time to time, such as for charging a battery of an implantable component or another useful purpose. Patients suffering from certain medical conditions may benefit from such "on-demand" application of electrical tissue stimulation. Examples of such medical conditions may include epilepsy, depression, post-stroke paralysis, migraines, angina, obesity, tinnitus, digestive tract disorders, bladder incontinence, obsessive-compulsive disorder, Tourette's syndrome, bulimia and other brain ailments, and erectile dysfunction.

Figure 3:
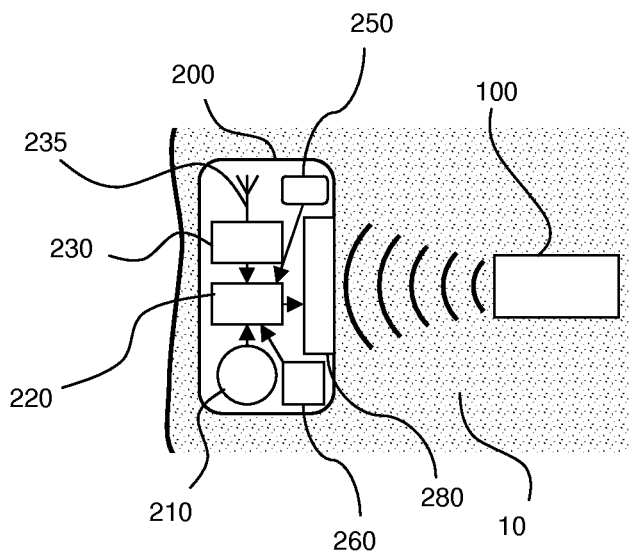
FIG. 3 shows a general schematic depiction of the system including an implanted transmitter and an implanted receiver.

FIG. 3 shows an implantable embodiment of the transmitter 200, which may include the following additional optional elements:
- one or multiple sensors 250 including for example ECG or motion sensors, which may be in direct contact with tissue to detect the patient's electrocardiogram, pacing signals from conventional pacemakers, and other physiological parameters; such sensors being connected to their respective signal processing circuitry;
- a communications module 260 whose function is to provide a data path, for example by another RF communication, to and from an external control console (not shown) to allow the physician to turn the system on and off; set device parameters and to acquire diagnostic information about the patient and/or the device.

The transmitter 200 may be encased in a hermetically sealed housing constructed of a biologically compatible material, typical of currently existing pacemaker or ICD devices. Acoustically-transparent window may be incorporated in such housing to allow transmission of acoustic energy towards the receiver 100.

Figure 4:
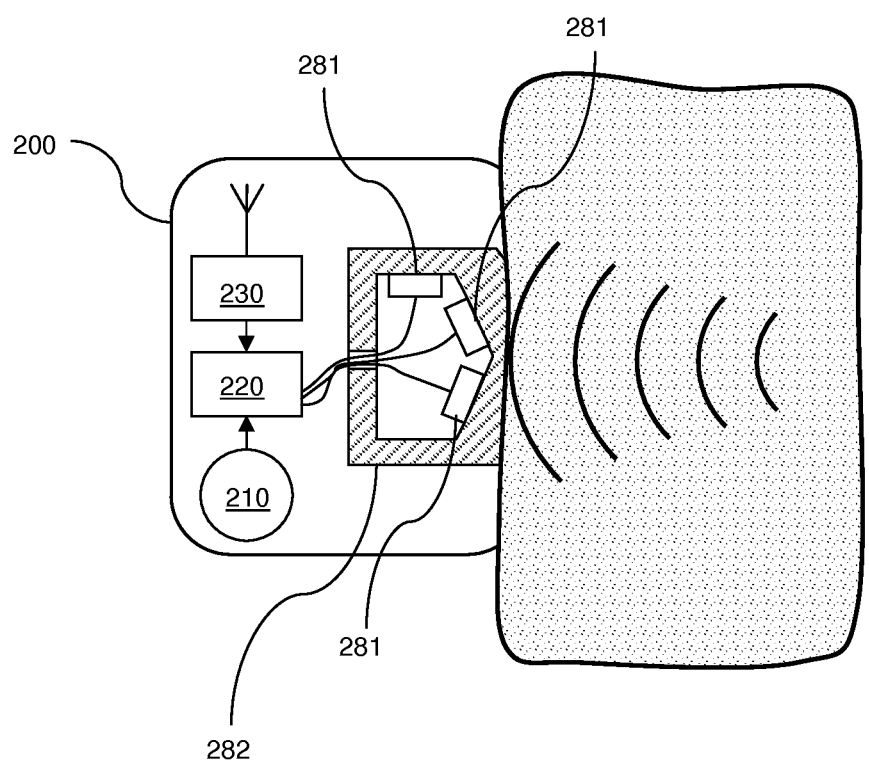
FIG. 4 is an example of an external TRA transmitter equipped with multiple transducers mounted in reverberator.
Figure 5:
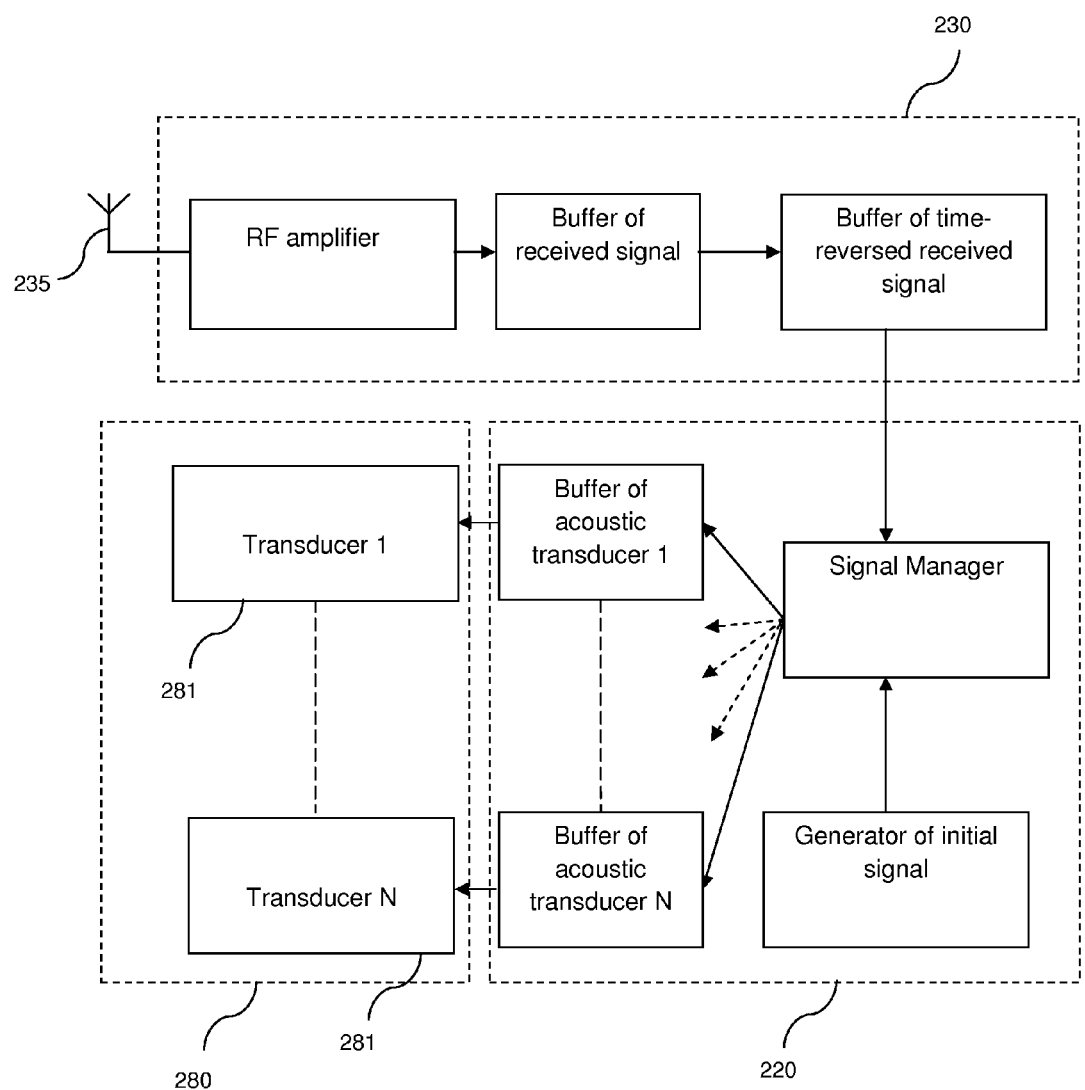
FIG. 5 shows a block-diagram of the TRA transmitter with multiple transducers as seen in FIG. 4.

Further details of the transmitter 200 are shown schematically in FIGS. 4 and 5—it comprises a TRA electronic unit 220 operably coupled to the emitting acoustic transducer 280. The system of the invention operates as follows. To establish the initial location of the receiver 100, the Generator of initial signal is activated to cause Signal Manager to send an initial signal through appropriate buffers to one or more emitting acoustic transducers 280 so as to send an initial generally unfocused acoustic signal towards the receiver 100. This signal is sent at sufficiently high level of power so as to reach the receiver 100. The receiver 100 generates an electromagnetic wave signal in response to the initial acoustic signal. Once this electromagnetic wave signal is received from the receiver 100 by the antenna 235 of the transmitter 200, it is amplified by the RF receiver 230, time-reversed and sent to Signal Manager. The signal is then stored in the memory of the electronic unit 220. It is then used to send a focused high intensity acoustic wave signal to receiver 100. The focused acoustic wave signal may have a lower overall level of energy than the initial unfocused signal but due to its highly focused nature it allows to fully energize the internal electrical circuit of the receiver 100.

The implantable receiver 100 of the system may move inside the body of the patient. Such movement may be caused by heart contractions, by breathing, peristalsis or by other shifts in the tissues. The movement may also be caused by the motion of the patient. When the receiver 100 is moved away from its original position, the acoustic energy transmission to the receiver 100 may be diminished. To compensate for this, the system of the invention may be configured to periodically update the driving signal and refocus the acoustic waveform on the current location of the receiver 100. Such refocusing operation may be triggered based on predetermined criteria, such as on a periodic basis or when decrease in acoustic signal amplitude is detected. Depending on the application, the frequency of update for the driving signal may be selected to be 10 seconds (for applications where no tissue motion or slow tissue motion is anticipated) or faster. For example, if the receiver is used as a cardiac stimulator, the updated signal may be generated every 0.1 to 1.0 seconds. Alternatively, continuous monitoring of the acoustic amplitude may be used to trigger an update in the driving signal when such amplitude falls below a predetermined threshold, for example below 80% of the maximum value or below a preselected absolute level assuring minimally acceptable performance of the system.

If more than one acoustic emitting transducer 281 is used to cumulatively energize the receiver 100, initial TRA feedback may be obtained for each of the transducers 281 individually. The Generator of initial signal sends this initial signal individually to each of the emitting acoustic transmitters 281 one at a time. Each transmitter 281 may then send the initial acoustic signal through the tissue such that the piezoelectric receiving transducer 120 of the receiver 100 receives it individually and also one at a time. These initial acoustic signals may then be transformed into an electromagnetic wave feedback signals and sent back by the antenna 150 of the receiver 100. The RF receiver 230 receives these electromagnetic wave feedback signals by its antenna 235 and sends them to the buffer of received signals. Once received, these signals are individually time-reversed by the TRA electronic unit as described in the cited previous patent applications. They may be then sent as individual driving signals to the respective buffer of each acoustic transducer. Once the operation of focusing acoustic signals is concluded for all emitting transducers 281, the respective TRA-generated driving signals may be sent to all transducers 281 simultaneously. As a result, a high level of superimposed acoustic energy may be closely focused on the area of the piezoelectric receiving transducer 120. High intensity acoustic energy is thereby sent only to the location of the wireless receiver 100 and not to the surrounding tissues.

Since TRA focusing of ultrasonic waves uses radiofrequency electromagnetic waves as a feedback signal for tuning the system, it is important to eliminate radiation of electromagnetic waves from any source other than the receiver 100. FIG. 4 shows an embodiment of the TRA focusing acoustic transducer 280 meeting this requirement of minimizing the radiation of electromagnetic waves during their operation. To achieve that goal and electromagnetically shield the transducers 281 and their connecting wires, the individual transducers 281 may be mounted inside a reverberator 282. The reverberator 282 may be preferably made of material with low attenuation of ultrasound, such as aluminum, to provide long reverberation time of acoustic signal in the body of the transmitter. Longer reverberation is important for the TRA mode of operation because it helps to accumulate more acoustic energy in time.

Figure 6:
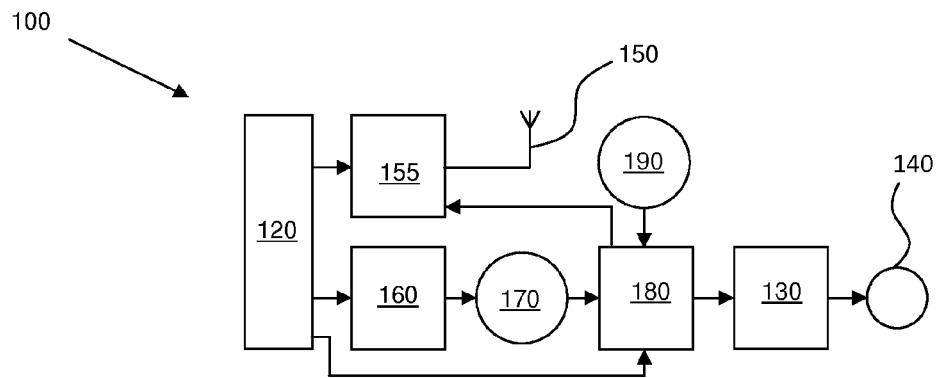
FIG. 6 shows a block-diagram of an implanted receiver containing a sensor to record physiologic or other useful data.

FIG. 6 shows yet another embodiment of the receiver 100, which may be equipped with at least one stimulating electrode 140 and at least one sensor 190 to measure a physiological or another useful parameter or signal as described above. In this case, a microprocessor 180 may be configured to collect data from the sensor 190 and to operate the stimulating electrode 140 via the internal electrical circuit (driver) 130. It may also be configured to send diagnostic and other pertinent data in a form of a radiofrequency signal to the transmitter 200. This signal may be amplified by the RF amplifier 155 and emitted by antenna 150. The microprocessor 180 may be powered by a battery 170, which may be optionally recharged by the internal charger 160 powered by the acoustic energy received by the receiving piezoelectric transducer 120. The receiving piezoelectric transducer 120 is operably coupled to the emitting antenna 150 via an RF amplifier 155 to send a radiofrequency feedback signal reflecting its received acoustic wave signals.

Figure 7:
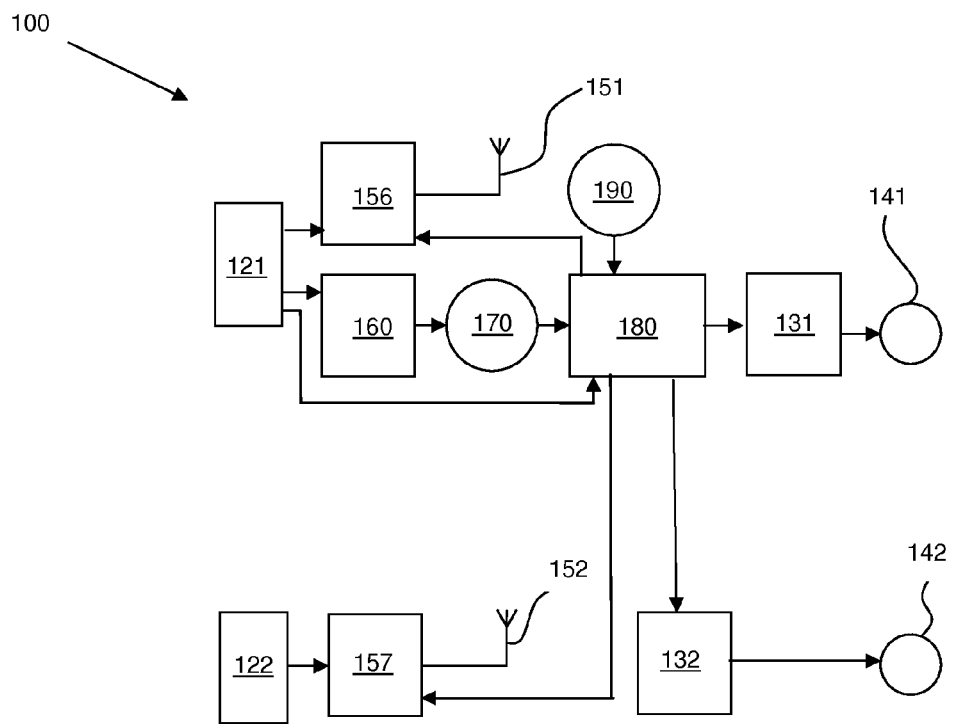
FIG. 7 is a block-diagram of a receiver containing several transducers, electrodes and sensors.

FIG. 7 shows a further design of the receiver 100 including more than one receiving transducer and electrode. Although an example having two receiving transducers, two stimulating electrodes and one sensor is shown in FIG. 7, the invention encompasses embodiments in which further additional receiving transducers, stimulating electrodes and sensors may be included as part of the receiver 100. These configurations allow greater flexibility of the system, in which different electrical signals are individually received from respective receiving transducers and directed to energize various desired stimulating electrodes.

Provided in the receiver 100 shown in FIG. 7 are the first receiving transducer 121 and the second receiving transducer 122. Each transducer 121 and 122 are connected via a corresponding RF amplifier 156 and 157 to a corresponding emitting antenna 151 and 152. If more than one stimulating electrode is used, each electrode (141 and 142 for example) may be equipped with a dedicated signal conditioner (131 and 132 in this case). The entire operation may be controlled by a central microprocessor 180.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A time-reversal acoustics system for remote generation of electrical signal in tissue, the system comprising:
    a first receiver including in a hermetically sealed housing:
        a first piezoelectric receiving transducer,
        an internal electrical circuit with an input operably coupled to said first receiving transducer,
        a first antenna configured for emitting a first radiofrequency signal, said first antenna operably coupled to said first receiving transducer, a first stimulating electrode operably coupled to an output of said internal electrical circuit, said first stimulating electrode is configured to be engaged with the tissue, and a transmitter including:

a time-reversal electronic unit, a radiofrequency signal receiver with an input operably coupled with a radiofrequency antenna and an output operably coupled with an input of said time-reversal electronic unit, an emitting acoustic transducer with an input operably coupled to an output of said time-reversal electronic unit, wherein said time-reversal electronic unit is configured to provide said emitting acoustic transducer with a driving signal formed by time-reversing of the radiofrequency signal received from said first receiver in response to an acoustic wave signal generated by said emitting acoustic transducer; said driving signal causing said emitting acoustic transducer to send a high intensity acoustic wave signal focused on said first piezoelectric receiving transducer to generate electrical energy sufficient to operate said first stimulating electrode to generate said electrical signal in the tissue.

2. The time-reversal acoustics system as in claim 1, wherein said transmitter is enclosed in a hermetically sealed housing and configured for implantation inside the patient.

3. The time-reversal acoustics system as in claim 2, wherein said transmitter is battery-powered.

4. The time-reversal acoustics system as in claim 2, wherein said system further includes an outside control console configured to communicate with said transmitter to send control signals thereto.

5. The time-reversal acoustics system as in claim 1, wherein said transmitter is configured to be externally placed in contact with the patient.

6. The time-reversal acoustics system as in claim 1, wherein said transmitter includes a reverberator.

7. The time-reversal acoustics system as in claim 6, wherein said transmitter includes a plurality of emitting transducers mounted inside said reverberator.

8. The time-reversal acoustics system as in claim 1, wherein said system includes additional receivers, each of the additional receivers including at least one respective receiving piezoelectric transducer and at least one corresponding antenna operably coupled thereto and configured for emitting radiofrequency signals.

9. The time-reversal acoustics system as in claim 1, wherein said receiver includes a plurality of stimulating electrodes operably coupled with said internal electrical circuit.

10. The time-reversal acoustics system as in claim 1, wherein said receiver includes a plurality of piezoelectric receiving transducers, each said receiving piezoelectric transducer is operably coupled to a respective antenna configured for emitting radiofrequency signals.

11. The time-reversal acoustics system as in claim 1, wherein said receiver includes at least one sensor.

12. The time-reversal acoustics system as in claim 11, wherein said sensor is selected from a group of sensors consisting of an ECG or other electrical activity sensor; a motion detector; a local, core body or other temperature sensor; a pressure sensor; an impedance sensor; a sensor to indicate rejection of a transplanted organ; a heart rhythm sensor; a force sensor; a chemical substance detector; and a sensor indicating remaining electrical charge level for an internal battery.

13. The time-reversal acoustic system as in claim 1, wherein said receiver and said transmitter are further configured to perform together a function of tissue stimulation, said function of tissue stimulation is selected from a group consisting of a cardiac stimulator, a pacemaker, a cardiac defibrillator, and a neurostimulator.

\* \* \* \* \*